(12) United States Patent
Emken et al.

(10) Patent No.: US 10,912,498 B2
(45) Date of Patent: *Feb. 9, 2021

(54) FLUORESCENCE-BASED SENSOR WITH MULTIPLE INDICATOR GRAFTS

(71) Applicant: Senseonics, Incorporated, Germantown, MD (US)

(72) Inventors: Jeremy Emken, Germantown, MD (US); Philip Huffstetler, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/132,615

(22) Filed: Sep. 17, 2018

(65) Prior Publication Data

US 2019/0015021 A1 Jan. 17, 2019

Related U.S. Application Data

(63) Continuation of application No. 14/541,987, filed on Nov. 14, 2014, now Pat. No. 10,080,514.

(60) Provisional application No. 61/904,759, filed on Nov. 15, 2013.

(51) Int. Cl.
| | |
|---|---|
| *A61B 5/1455* | (2006.01) |
| *A61B 5/145* | (2006.01) |
| *G01N 21/64* | (2006.01) |
| *A61B 5/00* | (2006.01) |
| *A61B 5/1473* | (2006.01) |

(Continued)

(52) U.S. Cl.
CPC ........ *A61B 5/14503* (2013.01); *A61B 5/0031* (2013.01); *A61B 5/1451* (2013.01); *A61B 5/1459* (2013.01); *A61B 5/14532* (2013.01); *A61B 5/14556* (2013.01); *A61B 5/14735* (2013.01); *A61B 5/6861* (2013.01); *G01N 21/27* (2013.01); *G01N 21/645* (2013.01); *A61B 5/1473* (2013.01); *A61B 2560/0219* (2013.01); *A61B 2560/0247* (2013.01); *G01N 2021/6421* (2013.01); *G01N 2021/6441* (2013.01)

(58) Field of Classification Search
None
See application file for complete search history.

(56) References Cited

U.S. PATENT DOCUMENTS

| | | |
|---|---|---|
| 5,512,246 A | 4/1996 | Russell et al. |
| 5,517,313 A | 5/1996 | Colvin, Jr. |
| 2004/0161853 A1 | 8/2004 | Yang et al. |

(Continued)

FOREIGN PATENT DOCUMENTS

EP 1 653 222 A1 5/2006

*Primary Examiner* — Marjan Fardanesh
(74) *Attorney, Agent, or Firm* — Rothwell, Figg, Ernst & Manbeck, P.C.

(57) ABSTRACT

A system including a sensor and a transceiver and configured to determine a concentration of an analyte in a medium of a living animal. The sensor may include first and second signal photodetectors and first and second reference photodetectors, which may each be covered by an associate filter. The first photodetector may receive light emitted from first and second grafts, respectively. The grafts may receive excitation light from one or more light sources. The transceiver may receive signals from the photodetectors of the sensor and may determine the analyte concentration based on the received signals.

19 Claims, 1 Drawing Sheet

(51) Int. Cl.
*A61B 5/1459* (2006.01)
*G01N 21/27* (2006.01)

(56) References Cited

U.S. PATENT DOCUMENTS

| | | |
|---|---|---|
| 2006/0052782 A1 | 3/2006 | Morgan et al. |
| 2008/0108885 A1 | 5/2008 | Colvin, Jr. |
| 2010/0073669 A1 | 3/2010 | Colvin, Jr. et al. |
| 2013/0211213 A1 | 8/2013 | DeHennis et al. |
| 2013/0324819 A1 | 12/2013 | Colvin, Jr. |

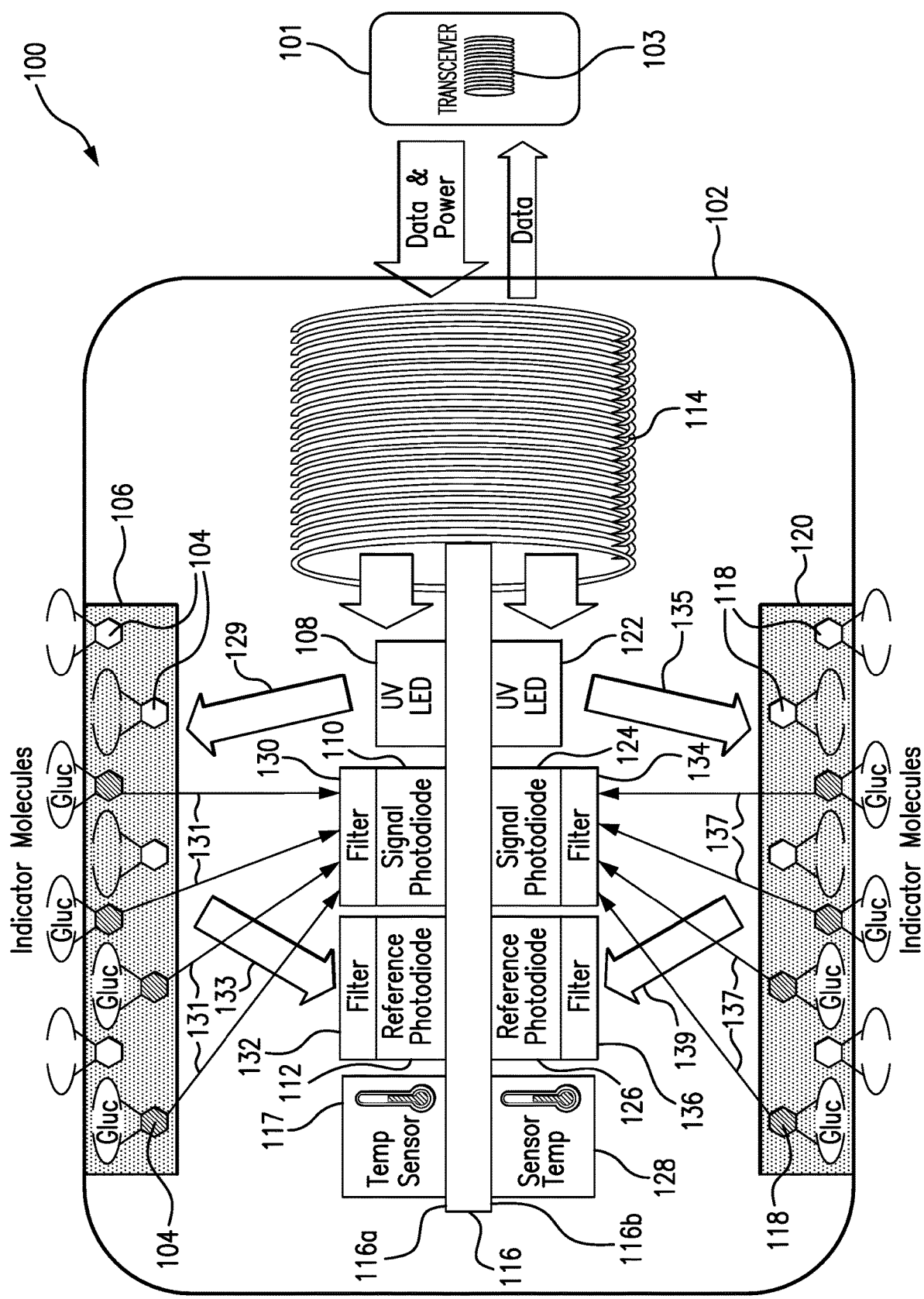

FLUORESCENCE-BASED SENSOR WITH MULTIPLE INDICATOR GRAFTS

CROSS-REFERENCE TO RELATED APPLICATION

The present application is a continuation of U.S. patent application Ser. No. 14/541,987, filed on Nov. 14, 2014, which claims the benefit of priority to U.S. Provisional Application Ser. No. 61/904,759, filed on Nov. 15, 2013, which are incorporated by reference in their entireties.

BACKGROUND

Field of Invention

The present invention relates generally to determining a concentration of an analyte in a medium of a living animal using a system including a sensor. Specifically, the present invention relates to a sensor that utilizes multiple sets of light sources, photodetectors, and grafts containing one or more fluorescent indicators to improve measurement accuracy by separately stimulating the indicators and quantifying light in one or more wavebands.

Discussion of the Background

A sensor may be implanted within a living animal (e.g., a human) and used to measure the concentration of an analyte in a medium (e.g., interstitial fluid (ISF), blood, or intraperitoneal fluid) within the living animal. The sensor may include a light source (e.g., a light-emitting diode (LED) or other light emitting element), indicator molecules in a graft, and a photodetector (e.g., a photodiode, phototransistor, photoresistor or other photosensitive element). Examples of implantable sensors employing indicator molecules to measure the concentration of an analyte are described in U.S. Pat. Nos. 5,517,313 and 5,512,246, which are incorporated herein by reference in their entirety.

The sensor may include a signal photodetector and a reference photodetector with associated filters. One filter may allow light emitted (e.g., fluoresced) by the indicator molecules to pass through so that the signal photodetector detects the amount of light emitted by the indicator molecules. Another filter may allow reference light having the wavelength of the excitation light emitted by the light source to pass through so that the reference photodetector detects an amount of reference light.

The light source may generate light within a small spectrum, the spectrum may overlap with the spectrum of light emitted by the indicator molecules. In other words, the light emitted by the indicator molecules and the light emitted by the light source are not independent of one another, and the light emitted by the light source may directly affect the detection of the light emitted by the indicator molecules.

Furthermore, the wavelength of the light that is absorbed by the indicator molecules for excitation may be close to the wavelength of the light emitted by the indicator molecules, and, therefore, it may be difficult to build filters that isolate the excitation light and not the light emitted by the indicator molecules (and vice versa). In fact, as no filter design is perfect for filtering light in narrow bands, there is always some cross talk or some light leakage causing undesirable effects. Because the wavelengths are similar, distinguishing between the two types of light can be difficult.

The signal photodetector and the reference photodetector may each receive both excitation light and light emitted by the indicator molecules. For instance, when the reference photodetector detects an increase in excitation light, a corresponding increase may be detected by the signal photodetector. Similarly, when the signal photodetector detects an increase in light emitted by the indicator, a corresponding increase may be detected by the reference photodetector. When this occurs, it may be difficult to accurately quantify the light coming from the indicator.

Also, the fluorescence lifetime of the indicator molecules may be short (e.g., less than a few microseconds). As a result, it may not be possible to detect the light emitted by the indicator molecules after extinguishing the light source and with no optical interference from the excitation light, as may be possible with indicator molecules having a longer fluorescence lifetime (e.g., a few milliseconds).

There is presently a need in the art for a more accurate sensor capable of determining analyte concentration in a medium of a living animal.

SUMMARY

One aspect of the invention may provide an optical sensor. The sensor may include a sensor housing, a first graft, first indicator molecules, a second graft, second indicator molecules, a substrate, a first light source, a first signal photodetector, a first reference photodetector, a second light source, a second signal photodetector, and a second reference photodetector. The first graft may cover at least a first portion of the sensor housing. The first indicator molecules may be embedded in the first graft and have a first optical characteristic responsive to the concentration of the analyte. The second graft may cover at least a second portion of the sensor housing. The second indicator molecules may be embedded in the second graft and have a second optical characteristic responsive to the concentration of the analyte. The first light source may be fabricated in or mounted on the substrate and may be configured to emit first excitation light to the first indicator molecules in the first graft. The first signal photodetector may be fabricated in or mounted on the substrate and may be configured to receive first emission light emitted by the first indicator molecules. The first reference photodetector may be fabricated in or mounted on the substrate and may be configured to receive first reference light. The second light source may be fabricated in or mounted on the substrate and may be configured to emit second excitation light to the second indicator molecules in the second graft. The second signal photodetector fabricated in or mounted on the substrate and may be configured to receive second emission light emitted by the second indicator molecules. The second reference photodetector may be fabricated in or mounted on the substrate and may be configured to receive second reference light.

In some embodiments, the first reference light may be the first excitation light emitted by the first light source, and the second reference light may be the second excitation light emitted by the second light source.

In some embodiments, the sensor includes a first signal filter, a first reference filter, a second signal filter, and a second reference filter. The first signal filter may be configured to pass only a first narrow band of wavelengths including the wavelength of the first emission light emitted by the first indicator molecules. The first signal filter may cover a light receiving surface of the first signal photodetector. The first reference filter may be configured to pass only a second narrow band of wavelengths including the wavelength of the first reference light. The first reference filter may cover a light receiving surface of the first reference photodetector. The second signal filter may be configured to pass only a third narrow band of wavelengths including the wavelength of the second emission light emitted by the second indicator molecules. The second signal filter may cover a light receiving surface of the second signal photodetector. The second reference filter may be configured to pass only a fourth narrow band of wavelengths including the wavelength of the second reference light. The second reference filter may cover a light receiving surface of the second reference photodetector.

In some embodiments, the first reference light may be the first excitation light emitted by the first light source, and the second reference light may be the second excitation light emitted by the second light source. In some embodiments, the wavelength of the first emission light emitted by the first indicator molecules may be different than the wavelength of the second emission light emitted by the second indicator molecules.

In some embodiments, the first indicator molecules may be different than the second indicator molecules, and the wavelength of the first emission light emitted by the first indicator molecules may be different than the wavelength of the second emission light emitted by the second indicator molecules.

In some embodiments, the sensor may include an inductive element configured to convey signals generated by the first signal photodetector, the first reference photodetector, the second signal photodetector, and the second reference photodetector.

In some embodiments, the sensor may include a temperature sensor. In some embodiments, the sensor may include a first temperature sensor fabricated in or mounted on the substrate, and a second temperature sensor fabricated in or mounted on the substrate.

In some embodiments, the wavelength of the first excitation light emitted by the first light source may be different than the wavelength of the second excitation light emitted by the second light source.

In some embodiments, the sensor housing may have a first side and a second side opposite the first side. The first portion may be a portion of the first side of the sensor housing. The second portion may be a portion of the second side of the sensor housing. The substrate may have a first side and a second side opposite the first side of the substrate. The first light source may be fabricated in or mounted on the first side of the substrate. The first signal photodetector may be fabricated in or mounted on the first side of the substrate. The first reference photodetector may be fabricated in or mounted on the first side of the substrate. The second light source may be fabricated in or mounted on the second side of the substrate. The second signal photodetector fabricated in or mounted on the second side of the substrate. The second reference photodetector may be fabricated in or mounted on the second side of the substrate.

In some embodiments, the substrate may have a first side and a second side opposite the first side of the substrate, and the first and second light sources, first and second signal photodetectors, first and second reference photodetectors may be fabricated in or mounted on the first side of the substrate.

Another aspect of the invention may provide a system for determining a concentration of an analyte in a medium of a living animal. The system may include an optical sensor and a transceiver. The optical sensor may be for implantation within the living animal. The sensor may include a sensor housing, a first graft, first indicator molecules, a second graft, second indicator molecules, a substrate, a first light source, a first signal photodetector, a first reference photodetector, a second light source, a second signal photodetector, and a second reference photodetector. The first graft may cover at least a first portion of the sensor housing. The first indicator molecules may be embedded in the first graft and have a first optical characteristic responsive to the concentration of the analyte. The second graft may cover at least a second portion of the sensor housing. The second indicator molecules may be embedded in the second graft and have a second optical characteristic responsive to the concentration of the analyte. The first light source may be fabricated in or mounted on the substrate and may be configured to emit first excitation light to the first indicator molecules in the first graft. The first signal photodetector may be fabricated in or mounted on the substrate and may be configured to receive first emission light emitted by the first indicator molecules. The first reference photodetector may be fabricated in or mounted on the substrate and may be configured to receive first reference light. The second light source may be fabricated in or mounted on the substrate and may be configured to emit second excitation light to the second indicator molecules in the second graft. The second signal photodetector fabricated in or mounted on the substrate and may be configured to receive second emission light emitted by the second indicator molecules. The second reference photodetector may be fabricated in or mounted on the substrate and may be configured to receive second reference light. The transceiver may be configured to receive the signals indicative of the first signal light, first reference light, second signal light, second reference light and to calculate a concentration of the analyte in the medium of the living animal based on the received signals.

Further variations encompassed within the systems and methods are described in the detailed description of the invention below.

BRIEF DESCRIPTION OF THE DRAWINGS

The accompanying drawing, which is incorporated herein and forms part of the specification, illustrates a non-limiting embodiment of the present invention.

FIG. 1 is a schematic, section view illustrating a sensor system embodying aspects of the present invention.

DETAILED DESCRIPTION OF PREFERRED EMBODIMENTS

FIG. 1 is a schematic view of a sensor system embodying aspects of the present invention. In one non-limiting embodiment, the system includes a sensor 100 and an external transceiver 101. In the embodiment shown in FIG. 1, the sensor 100 may be implanted in a living animal (e.g., a living human). The sensor 100 may be implanted (i.e., inserted), for example, in a living animal's arm, wrist, leg, abdomen, peritoneum, or other region of the living animal suitable for sensor implantation. For example, in one non-limiting embodiment, the sensor 100 may be implanted beneath the skin (i.e., in subcutaneous tissues). In some embodiments, the sensor 100 may be an optical sensor (e.g., a fluorometer). The system including the sensor 100 may be configured to determine a concentration of an analyte (e.g., glucose or oxygen) in a medium (e.g., interstitial fluid or blood) of the living animal. In some embodiments, the sensor 100 may be a chemical or biochemical sensor. In some embodiments, the sensor 100 may be a fluorometer. In one non-limiting embodiment, the sensor 100 may be designed to last for up to six months or longer in the living animal before being replaced.

The external transceiver 101 may be an electronic device that communicates with the sensor 100 to power the sensor 100 and/or receive measurement information (e.g., photodetector and/or temperature sensor readings) from the sensor 100. The measurement information may include one or more readings from one or more photodetectors of the sensor and/or one or more readings from one or more temperature sensors of the sensors. In some embodiments, the transceiver 101 may calculate analyte (e.g., glucose) concentrations from the measurement information received from the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two to five minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a reading from the sensor 100.

In some embodiments, the transceiver 101 may include an inductive element 103, such as, for example, a coil. The transceiver 101 may generate an electromagnetic/electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the sensor reader 101 may convey data by modulating the electromagnetic wave used to power the sensor 100 (e.g., by modulating the current flowing through a coil of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the sensor transceiver 101 may receive data by detecting modulations in the electromagnetic wave generated by the sensor 100, e.g., by detecting modulations in the current flowing through a coil 103 of the sensor reader 101.

The inductive element 103 of the transceiver 101 and the inductive element 114 of the sensor 100 may be in any configuration that permits adequate field strength to be achieved when the two inductive elements are brought within adequate physical proximity.

In one non-limiting embodiment, sensor 100 includes a sensor housing 102 (i.e., body, shell, capsule, or encasement), which may be rigid and/or biocompatible. In exemplary embodiments, sensor housing 102 may be formed from a suitable, optically transmissive polymer material, such as, for example, acrylic polymers (e.g., polymethylmethacrylate (PMMA)) or silicone-based polymers. In some embodiments, the sensor housing 102 may any shape suitable for implantation into a living animal. For instance, in some non-limiting embodiments, the sensor housing 102 may be cylindrical, pill-shaped, disc-shaped, spherical, or rectangular prism-shaped.

In some embodiments, the sensor 100 may include a substrate 116. The substrate 116 may include a first side 116a and a second side 116b. The second side 116b may be opposite the first side 116a.

In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components. In some embodiments, circuitry of the sensor 100 may incorporate some or all of the structure described in U.S. patent application Ser. No. 13/650,016, which is incorporated herein by reference in its entirety, with particular reference to FIG. 11D.

In some embodiments, the sensor 100 may include a first light source 108 and a second light source 122. The light sources 108 and 122 may be, for example, light emitting diodes (LEDs) or other light sources that emit radiation. Although not illustrated in FIG. 1, in some embodiments, sensor 100 may include additional light sources (e.g., third or third and fourth light sources, etc.). In a non-limiting embodiment, one or more of the light sources 108 and 122 may emit ultraviolet (UV) light (e.g., light with a wavelength of approximately 378 nm). In some embodiments, the first light source 108 and a second light source 122 may emit light having approximately the same wavelength, but this is not required, and, in other embodiments, the first and second light sources 108 and 122 may emit light having different wavelengths.

In some embodiments, the first and second light sources 108 and 122 may be fabricated in or mounted on opposite sides of the substrate 116. For example, as illustrated in FIG. 1, the first light source 108 may be fabricated in or mounted on first side 116a of substrate 116, and the second light source 122 may be fabricated in or mounted on second side 116b of substrate 116. In embodiments where the first light source 108 and/or the second light source 122 are mounted on the substrate 116, the first light source 108 and/or the second light source 122 may be flip-chip mounted on the semiconductor substrate 116.

In some embodiments, the sensor 100 may also include one or more photodetectors (e.g., photodiodes, phototransistors, photoresistors or other photosensitive elements). For example, as illustrated in FIG. 1, sensor 100 may have a first signal photodetector 110, a first reference photodetector 112, a second signal photodetector 124, and a second reference photodetector 126. Although not illustrated in FIG. 1, in some embodiments, sensor 100 may include additional photodetectors (e.g., third and fourth signal photodetectors and/or third and fourth reference photodetectors). In some embodiments, the first signal photodetector 110 and first reference photodetector 112 may be a fabricated in or mounted on the first side 116a of the substrate 116. In some non-limiting embodiments, the second signal photodetector 124 and second reference photodetector 126 may be a fabricated in or mounted on the second side 116b of the substrate 116.

In some embodiments, the sensor 100 may include one or more temperature sensors (e.g., temperature transducers). Each of the one or more temperature sensors may generate a signal indicative of the temperature of the sensor 100. In some embodiments, the sensor 100 may include a first temperature sensor 117 and a second temperature sensor 128. In a non-limiting, exemplary embodiment, the temperature sensors 117 and 128 may be a band-gap based temperature transducers. However, in alternative embodiments, different types of temperature sensors may be used, such as, for example, thermistors or resistance temperature detectors. In some embodiments, as illustrated in FIG. 1, the first temperature sensor 117 may be fabricated in or mounted on the first side 116a of the substrate 116, and the second temperature sensor 128 may be fabricated in or mounted on the second side 116b of the substrate 116.

In some embodiments, sensor 100 may include one or more grafts or matrix layers (e.g., polymer grafts) coated, diffused, adhered, or embedded on or in portions of the exterior surface of the sensor housing 102. For example, in some embodiments, as illustrated in FIG. 1, the sensor 100 may include a first graft 106 and a second graft 120. However, in other embodiments, the sensor 100 may include more than two grafts. In other words, the sensor 100 may additionally include third, fourth, and/or more grafts. In some embodiments, the grafts 106 and 120 may be a fluorescent glucose indicating polymer. In one non-limiting embodiment, the polymer may be biocompatible and stable, grafted onto the surface of sensor housing 102, and designed to allow for the direct measurement of interstitial fluid (ISF) glucose after subcutaneous implantation of the sensor 100. In another non-limiting embodiment, the polymer may be adhered to one or more membranes that are attached to the sensor.

In some embodiments, indicator molecules may be distributed throughout the grafts. The indicator molecules may be fluorescent indicator molecules (e.g., Trimethyltriflurom-ethylsilane (TFM) fluorescent indicator molecules) or absorption indicator molecules. In some embodiments, the indicator molecules may reversibly bind an analyte (e.g., glucose). When an indicator molecule has bound the analyte, the indicator molecule may become fluorescent, in which case the indicator molecule may be capable of absorbing (or being excited by) excitation light and emitting emission light. In one non-limiting embodiment, the excitation light may have a wavelength of approximately 378 nm, and the emission light may have a wavelength in the range of 400 to 500 nm. When no glucose is bound, the indicator molecule may be only weakly fluorescent.

In some embodiments, as illustrated in FIG. 1, first graft 106 may include first indicator molecules 104, and second graft 120 may include second indicator molecules 118. The first indicator molecules 104 may have a first optical characteristic responsive to the concentration of the analyte, and the second indicator molecules 118 may have a second optical characteristic responsive to the concentration of the analyte. In some non-limiting embodiments the first indicator molecules 104 may be the same as the second indicator molecules 118. However, in some alternative embodiments, the first indicator molecules 104 may be different than the second indicator molecules 118. For example, in some non-limiting embodiments, the first indicator molecules 104 may be different than the second indicator molecules 118 in that the first indicator molecules 104 may be excited by excitation light having a wavelength (i.e., range of wavelengths) different than the wavelength (i.e., range of wavelengths) of the excitation light that excites the second indicator molecules. Further, in some non-limiting embodiments, the first indicator molecules 104 may, alternatively or additionally, be different than the second indicator molecules 118 in that the emission light 131 emitted by the first indicator molecules 104 may have a wavelength (i.e., range of wavelengths) different than the wavelength (i.e., range of wavelengths) of the emission light 137 emitted by the second indicator molecules 118. Also, in some embodiments, the first graft 106 and/or second graft 120 may include more than one type of indicator molecule.

In a non-limiting embodiment, the first graft 106 may be positioned to receive first excitation light 129 emitted by the first light source 108, and the second graft 120 may be positioned to receive second excitation light 135 emitted by light source 122. The first light source 108 may be configured to emit radiation 129 over a range of wavelengths that interact with the first indicator molecules 104, and the second light source 122 may be configured to emit radiation 135 over a range of wavelengths that interact with the second indicator molecules 118. In other words, the light source 108 may emit excitation light 129 that is absorbed by the first indicator molecules 104 in the first matrix layer/polymer graft 106, and the light source 122 may emit excitation light 135 that is absorbed by the second indicator molecules 118 in the second matrix layer/polymer graft 120.

In some embodiments, the first excitation light 129 emitted by first light source 108 may have a wavelength that is identical/substantially identical to the wavelength of the second excitation light 135 emitted by the second light source 122. However, in other embodiments, the first excitation light 129 emitted by first light source 108 may have a wavelength that is different than (i.e., not substantially identical to) the wavelength of the second excitation light 135 emitted by the second light source 122. In one non-limiting embodiment, one or more of the light sources 108 and 122 may emit excitation light at a wavelength of approximately 378 nm. In another non-limiting embodiment, one or more light source could emit excitation light in the UV range (~378 nm) and another light source could emit excitation light in the visible range (~400-700 nm), such as, for example, light in the ~500-700 nm (green, yellow, orange, red) range, which may be outside the range of light emitted by the first indicator molecules 104 and/or second indicator molecules 118.

In some embodiments, the sensor 100 may include one or more filters. Each filter may be configured to allow only a certain subset of wavelengths of light to pass through. In some embodiments, each filter may cover one or more photodetectors. In some embodiments, the filters may be thin film (dichroic) filters deposited on glass and may pass only a narrow band of wavelengths and otherwise reflect most of the light received thereby. In some embodiments, the filters may be thin film (dichroic) filters deposited directly onto the photo detectors and may pass only a narrow band of wavelengths and otherwise reflect most of the light received thereby.

In some non-limiting embodiments, the first signal photodetector 110 may be covered by a first signal filter 130. The first signal filter 130 may be configured to pass a narrow band of wavelengths including the wavelength of the first emission light 131 emitted (e.g., fluoresced) by the first indicator molecules 104 in the first graft 106. For instance, in one non-limiting embodiment, the peak emission of the first indicator molecules 104 may occur around 435 nm, and the first signal filter 130 may pass light in the range of 400-500 nm and prevent other light from reaching the first signal photodetector 110 (e.g., by reflecting most of the light outside the 400-500 nm range). However, this is not required, and, in other embodiments, the first emission light 131 may have a different peak emission wavelength, and/or the first signal filter 130 may pass light in a different (e.g., narrower, expanded, or shifted) wavelength range.

In some non-limiting embodiments, the first reference photodetector 112 may be covered by a first reference filter 132. The first reference filter 132 may be configured to pass a narrow band of wavelengths including the wavelength of a first reference light 133. In one non-limiting embodiment, the first reference light 133 passed by the first reference filter 132 may have the same wavelength as the first excitation light 129 (e.g., 378 nm), and the first reference filter 132 may pass light in a narrow band (e.g., 350-400 nm) including the wavelength of the first excitation light 129 and prevent other light from reaching the first reference photodetector 112. However, this is not required, and, in other embodiments, the first reference light 133 passed by the first reference filter 132 may have a different wavelength than the first excitation light 129 (e.g., the wavelength of light emitted by reference indicator molecules that are unaffected or generally unaffected by the presence and/or concentration of the analyte), and/or the first reference filter 132 may pass light in a different (e.g., narrower, expanded, or shifted) wavelength range.

In some non-limiting embodiments, the second signal photodetector 124 may be covered by a second signal filter 134. The second signal filter 134 may be configured to pass a narrow band of wavelengths including the wavelength of the second emission light 137 emitted (e.g., fluoresced) by the second indicator molecules 118 in the second graft 120. In some embodiments, the wavelength of the second emission light 137 may be the same as the wavelength of the first emission light 131 emitted (e.g., fluoresced) by the first indicator molecules 104 in the first graft 106, and the second signal filter 134 may be configured to pass the same narrow band of wavelengths as is passed by the first signal filter 130. That is, in some embodiments, the second signal filter 134 may be identical to the first signal filter 130.

However, in other embodiments, the wavelength of the second emission light 137 may be different than the wavelength of the first emission light 131, and the second signal filter 134 may be configured to pass a different narrow band of wavelengths than the first signal filter 130.

In some non-limiting embodiments, the second reference photodetector 126 may be covered by a second reference filter 128. The second reference filter 128 may be configured to pass a narrow band of wavelengths including the wavelength of a second reference light 139. In one non-limiting embodiment, the second reference light 139 passed by the second reference filter 134 may have the same wavelength as the second excitation light 129, and the second reference filter 134 may pass light in a narrow band including the wavelength of the second excitation light 135 and prevent other light from reaching the second reference photodetector 126. However, this is not required, and, in other embodiments, the second reference light 139 passed by the second reference filter 136 may have a different wavelength than the second excitation light 135 (e.g., the wavelength of light emitted by reference indicator molecules that are unaffected or generally unaffected by the presence and/or concentration of the analyte), and/or the second reference filter 136 may pass light in a different (e.g., narrower, expanded, or shifted) wavelength range.

The first signal photodetector 110 may be configured to (a) receive the first emission light 131 that is emitted from the first indicator molecules 104 in the first graft 106 and (b) generate a signal indicative of the amount of light received thereby. In some embodiments, higher analyte (e.g., glucose or oxygen) levels/concentrations correspond to a greater amount of first emission light 131 (e.g., fluorescence) of the first indicator molecules 104 in the first graft 106, and, therefore, a greater number of photons striking the first signal photodetector 110.

The first reference photodetector 112 may be configured to receive the first reference light 133 and generate a signal indicative of the amount of light received thereby. In some embodiments, the first reference light 133 may have the same wavelength as the first excitation light 129 emitted by the first light source 108 and, as illustrated in FIG. 1, may include a portion of the first excitation light 129 that is reflected from the first graft 106.

The second signal photodetector 124 may be configured to (a) receive the second emission light 137 that is emitted from the second indicator molecules 118 in the second graft 120 and (b) generate a signal indicative of the amount of light received thereby. In some embodiments, higher analyte (e.g., glucose or oxygen) levels/concentrations correspond to a greater amount of second emission light 137 (e.g., fluorescence) of the second indicator molecules 118 in the second graft 120, and, therefore, a greater number of photons striking the second signal photodetector 124.

The second reference photodetector 126 may be configured to receive the second reference light 139 and generate a signal indicative of the amount of light received thereby. In some embodiments, the second reference light 139 may have the same wavelength as the second excitation light 135 emitted by the second light source 122 and, as illustrated in FIG. 1, may include a portion of the second excitation light 135 that is reflected from the second graft 120.

In some embodiments, the first light source 108 may emit excitation light 129 to the first indicator molecules 104 in first graft 106, and the first indicator molecules 104 may react and emit an amount of first emission light 131 that corresponds to the amount of binding between the first indicator molecules 104 and analyte. The first signal photodetector 110 and first reference photodetector 112, which receive first emission light 131 and first reference light 133, respectively, may provide a signal channel and a reference channel, respectively.

The second light source 122 may emit excitation light 135 to the second indicator molecules 118 in second graft 120, and the second indicator molecules 118 react and emit an amount of second emission light 137 that corresponds to the amount of binding between the second indicator molecules 118 and analyte. The second signal photodetector 124 and second reference photodetector 126, which receive second emission light 137 and second reference light 139, respectively, may provide an additional signal channel and an additional reference channel, respectively. In some embodiments, one or more additional light sources (e.g., a third light source of third and fourth light sources), one or more additional pairs of signal and reference photodetectors (e.g., third signal and reference photodetectors and/or a fourth signal and reference photodetectors), and/or one or more additional grafts may provide one or more additional signal and reference channels.

Relative to a sensor having only a single signal channel and a single reference channel, the additional channels may provide additional information to reduce noise or improve accuracy. More information regarding the response of the sensor to various analyte levels may lower the error levels and improve the accuracy of measuring the analyte in users with implanted sensors. Any overlap between the information from the different channels could be quantized as more statistically significant readings and increased accuracy may result.

Although it is not necessary to use different indicator molecules for the first and second grafts 106 and 120, if two identical grafts were used, the overlap of data could be identical, and any errant readings may not be negated. However, even if two identical grafts that did not provide a large amount of new information were used, the sensor 100 would still essentially have a second channel that could give additional information to help reduce noise and improve accuracy Nonetheless, in preferred embodiments, the first indicator molecules 104 of the first graft 106 are different than the second indicator molecules 118 of the second graft 120 (e.g., the peak wavelength of the first emission light 131 of the first indicator molecules 104 may be different than the peak wavelength of the second emission light 137 of the second indicator molecules 118). The overlap of spectrums may be suggestive that the analyte readings would be much more likely to fall within the overlap between the information from the different channels, effectively increasing the accuracy of analyte measurements.

Furthermore, regardless of whether the first indicator molecules 104 of the first graft 106 and the second indicator molecules 118 of the second graft 120 are different, the presence of two grafts may be an advantage because, in some embodiments, one graft may act as a backup in the event that the other is damaged or degraded (e.g., photobleached) and still provide useful data. For instance, in some non-limiting embodiments, the transceiver 101 may include circuitry (e.g., a processor with memory) that may be configured to determine the concentration of an analyte in the medium based on signals generated by the first signal photodetector and first reference photodetector if a signal generated by the second signal photodetector or a signal generated by the second reference photodetector is unavailable (e.g., because the graft 118 is damaged or degraded) and vice versa. In some embodiments, the transceiver 101 may determine that a graft is damaged or degraded based on signal acquisition/data processing across different analyte concentrations and, based on this determine, calculate analyte concentrations using only grafts that have not been determined to be damaged or degraded.

In some embodiments, the system including the sensor 100 may be used to obtain accurate interstitial fluid (ISF) analyte (e.g., glucose) readings in a living animal (e.g., a living human) in which the sensor 100 is implanted, and the transceiver 101 may include circuitry configured to determine the concentration of the analyte in the medium based on the signals generated by the photodetectors. In another embodiment, the system including the sensor 100 may be used to obtain accurate intraperitoneal fluid analyte (e.g., glucose) readings/measurements in a user implanted with the sensor. In yet another embodiment, system including the sensor 100 may be used to obtain accurate intravascular fluid or blood analyte (e.g., glucose) readings/measurements in a user. For instance, in some non-limiting embodiments, the transceiver 101 may be configured to determine the analyte concentration based on the signals generated by the first signal photodetector 110, first reference photodetector 112, second signal photodetector 124, and second reference photodetector 126.

Further, in some embodiments, the circuitry of the transceiver 101 may be configured to determine the analyte concentration based on a signal or signals generated by one or more temperature sensors. For instance, in one embodiment, the circuitry of the transceiver 101 may be configured to determine the analyte concentration based the signals generated by the first and second temperature sensors 117 and 126. In some embodiments, the inductive element 118 may be configured to convey the determined analyte concentration.

In some embodiments, the sensor 100 including more than one light source, graft, signal photodetector, and reference photodetector may be larger than the size of a similar sensor having only one light source, graft, signal photodetector, and reference photodetector. However, this is not required, and, in some alternative embodiments, the sensor 100 including more than one light source, graft, signal photodetector, and reference photodetector may be no larger than the size of a similar sensor having only one light source, graft, signal photodetector, and reference photodetector. For instance, in one non-limiting embodiment, the additional light source, signal photodetector, and reference photodetector may be located within the sensor housing 102 in a portion of the sensor that would have been filled with a clear encapsulating material (e.g., epoxy) if the additional components had not been provided. In other words, the additional light source, graft, signal photodetector, and reference photodetector may increase the overall accuracy of the sensor without increasing the size of the sensor.

Although embodiments have been described in which the first light source 108, first signal photodetector 110, and first reference photodetector 112 are fabricated in or mounted on one side of the substrate 116 (e.g., first side 116a) and the second light source 122, second signal photodetector 124, and second reference photodetector 126 are fabricated in or mounted on the opposite side of the substrate 116 (e.g., second side 116a), this is not required. For example, in some alternative embodiments, the first and second light sources 108 and 122, first and second signal photodetectors 110 and 124, and first and second reference photodetectors 112 and 126 may be fabricated in or mounted on the same side of the substrate 116 (e.g., first side 116a).

Similarly, the first and second grafts 106 and 120, which may be positioned to receive first excitation light 129 emitted by the first light source 108 and second excitation light 135 emitted by light source 122, respectively, need not be located on opposite sides of the sensor housing 102 (relative to the substrate 116) as is illustrated in FIG. 1. For example, in some alternative embodiments, the first and second grafts 106 and 120 may be located on the same of the sensor housing 102 (relative to the substrate 116).

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, the circuitry of the sensor 100 may be implemented in hardware, software, or a combination of hardware and software. Similarly, the circuitry of the transceiver 101 may be implemented in hardware, software, or a combination of hardware and software. The software may be implemented as computer executable instructions that, when executed by a processor, cause the processor to perform one or more functions.

For another example, in one alternative embodiment, the sensor 100 may include multiple grafts, multiple signal photodetectors, and multiple reference photodetectors but may only include a single light source that is capable of illuminating the multiple grafts. Also, in another alternative embodiment, the sensor 100 may include more than two light sources and/or more than two grafts.

For still another example, although in some embodiments, as illustrated in FIG. 1, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

What is claimed is:

1. A system for determining a concentration of an analyte in a medium of a living animal, the system comprising:
    an optical sensor, the sensor including:
        a sensor housing;
        a first graft covering at least a first portion of the sensor housing;
        first indicator molecules embedded in the first graft and having a first optical characteristic responsive to the concentration of the analyte;
        a second graft covering at least a second portion of the sensor housing;
        second indicator molecules embedded in the second graft and having a second optical characteristic responsive to the concentration of the analyte;
        a substrate;
        a first light source fabricated in or mounted on the substrate and configured to emit first excitation light to the first indicator molecules in the first graft;
        a first signal photodetector fabricated in or mounted on the substrate and configured to receive first emission light emitted by the first indicator molecules and output a signal indicative thereof;
        a second light source fabricated in or mounted on the substrate and configured to emit second excitation light to the second indicator molecules in the second graft; and
        a second signal photodetector fabricated in or mounted on the substrate and configured to receive second emission light emitted by the second indicator molecules and output a signal indicative thereof; and
    a transceiver configured to:
        receive the signals indicative of the first signal light and the second signal light;
        determine whether the first graft is damaged or degraded using one or more of the received signals; and
        if the first graft is determined to be damaged or degraded, calculate a concentration of the analyte in the medium of the living animal based on the received signal indicative of the second signal light but not the received signal indicative of the first signal light.

2. The system of claim 1, wherein the sensor further comprises:
    a first signal filter configured to pass only a first narrow band of wavelengths including the wavelength of the first emission light emitted by the first indicator molecules, wherein the first signal filter covers a light receiving surface of the first signal photodetector; and
    a second signal filter configured to pass only a second narrow band of wavelengths including the wavelength of the second emission light emitted by the second indicator molecules, wherein the second signal filter covers a light receiving surface of the second signal photodetector.

3. The system of claim 2, wherein the wavelength of the first emission light emitted by the first indicator molecules is different than the wavelength of the second emission light emitted by the second indicator molecules.

4. The system of claim 1, wherein the first indicator molecules are different than the second indicator molecules, and the wavelength of the first emission light emitted by the first indicator molecules is different than the wavelength of the second emission light emitted by the second indicator molecules.

5. The system of claim 1, wherein the first indicator molecules are identical to the second indicator molecules, and the wavelength of the first emission light emitted by the first indicator molecules is the same as the wavelength of the second emission light emitted by the second indicator molecules.

6. The system of claim 1, wherein the sensor further comprises an inductive element configured to convey signals generated by the first signal photodetector and the second signal photodetector.

7. The system of claim 1, wherein the sensor further comprises a third signal photodetector fabricated in or mounted on the substrate and configured to receive third emission light.

8. The system of claim 7, wherein the sensor further comprises third indicator molecules embedded in the first graft and having a third optical characteristic responsive to the concentration of the analyte, and the third emission light is emitted by third indicator molecules embedded in the first graft.

9. The system of claim 7, wherein the sensor further comprises:
    a third graft covering at least a third portion of the sensor housing; and
    third indicator molecules embedded in the third graft and having a third optical characteristic responsive to the concentration of the analyte;
    wherein the third emission light is emitted by the third indicator molecules.

10. The system of claim 1, wherein the sensor further comprises a temperature sensor configured to output a temperature signal indicative of the temperature of the sensor, and the transceiver is further configured to receive the temperature signal and use the received temperature signal in the calculation of the analyte concentration.

11. The system of claim 1, wherein the sensor further comprises first and second temperature sensors configured to output first and second temperature signals, respectively, and the transceiver is further configured to receive the first and second temperature signals and use the received first and second temperature signals in the calculation of the analyte concentration.

12. The system of claim 1, wherein the transceiver is further configured to:
   determine whether the second graft is damaged or degraded using one or more of the received signals; and
   if the second graft is determined to be damaged or degraded, calculate a concentration of the analyte in the medium based on the received signal indicative of the first signal light but not the received signal indicative of the second signal light.

13. The system of claim 1, wherein:
   the sensor housing has a first side and a second side opposite the first side;
   the first portion is a portion of the first side of the sensor housing;
   the second portion is a portion of the second side of the sensor housing;
   the substrate has a first side and a second side opposite the first side of the substrate;
   the first light source is fabricated in or mounted on the first side of the substrate;
   the first signal photodetector is fabricated in or mounted on the first side of the substrate;
   the second light source is fabricated in or mounted on the second side of the substrate; and
   the second signal photodetector is fabricated in or mounted on the second side of the substrate.

14. The system of claim 1, wherein:
   the sensor housing has a first side and a second side opposite the first side;
   the second portion is a portion of the second side of the sensor housing;
   the substrate has a first side and a second side opposite the first side of the substrate; and
   the first light source, the first signal photodetector, the first reference photodetector, the second light source, the second signal photodetector, and the second reference photodetector are fabricated in or mounted on the first side of the substrate.

15. The system of claim 1, wherein the wavelength of the first excitation light emitted by the first light source is different than the wavelength of the second excitation light emitted by the second light source.

16. The system of claim 1, wherein the transceiver comprises an inductive element.

17. A method for determining a concentration of an analyte in a medium of a living animal, the method comprising:
   using a first signal photodetector to receive first emission light emitted by first indicator molecules of a first graft covering at least a first portion of a sensor housing of an optical sensor, wherein the first indicator molecules have a first optical characteristic responsive to the concentration of the analyte in the medium;
   using the first signal photodetector to output a signal indicative of an amount of the first emission light received by the first signal photodetector;
   using a second signal photodetector to receive second emission light emitted by second indicator molecules of a second graft covering at least a second portion of the sensor housing of the optical sensor, wherein the second indicator molecules have a second optical characteristic responsive to the concentration of the analyte in the medium;
   using the second signal photodetector to output a signal indicative of an amount of the second emission light received by the second signal photodetector;
   determining that the first graft is damaged or degraded using one or more of the received signals; and
   if the first graft is determined to be damaged or degraded, calculating a concentration of the analyte in the medium of the living animal based on the signal indicative of the second signal light but not the received signal indicative of the first signal light.

18. The method of claim 17, further comprising, before determining that the first graft is damaged or degraded, calculating a concentration of the analyte in the medium of the living animal based on the signals indicative of the first and second signal lights.

19. The method of claim 17, further comprising using a temperature sensor to output a temperature signal indicative of the temperature of the sensor, wherein the concentration of the analyte in the medium of the living animal is calculated based on the signal indicative of the second signal light and the temperature signal.

* * * * *